United States Patent
Kamei et al.

(10) Patent No.: US 11,389,389 B2
(45) Date of Patent: Jul. 19, 2022

(54) COSMETIC

(71) Applicant: SHIN-ETSU CHEMICAL CO., LTD., Tokyo (JP)

(72) Inventors: Masanao Kamei, Annaka (JP); Tomoya Kanai, Annaka (JP); Takuya Abe, Annaka (JP); Ryuichi Inaba, Ichikawa (JP); Tsuneo Kimura, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/635,068

(22) PCT Filed: Jun. 22, 2018

(86) PCT No.: PCT/JP2018/023822
§ 371 (c)(1),
(2) Date: Jan. 29, 2020

(87) PCT Pub. No.: WO2019/031079
PCT Pub. Date: Feb. 14, 2019

(65) Prior Publication Data
US 2020/0246246 A1     Aug. 6, 2020

(30) Foreign Application Priority Data
Aug. 10, 2017   (JP) .............................. JP2017-155287

(51) Int. Cl.
| | |
|---|---|
| *A61K 8/891* | (2006.01) |
| *A61K 8/02* | (2006.01) |
| *A61K 8/31* | (2006.01) |
| *A61K 8/34* | (2006.01) |
| *A61K 8/35* | (2006.01) |
| *A61K 8/37* | (2006.01) |
| *A61K 8/49* | (2006.01) |
| *A61Q 1/02* | (2006.01) |
| *A61Q 1/04* | (2006.01) |
| *A61Q 1/10* | (2006.01) |
| *A61Q 15/00* | (2006.01) |
| *A61Q 17/04* | (2006.01) |
| *A61Q 19/10* | (2006.01) |
| *A61Q 1/06* | (2006.01) |
| *A61Q 19/00* | (2006.01) |

(52) U.S. Cl.
CPC ............... *A61K 8/891* (2013.01); *A61K 8/02* (2013.01); *A61K 8/31* (2013.01); *A61K 8/34* (2013.01); *A61K 8/342* (2013.01); *A61K 8/35* (2013.01); *A61K 8/37* (2013.01); *A61K 8/496* (2013.01); *A61K 8/4966* (2013.01); *A61Q 1/02* (2013.01); *A61Q 1/04* (2013.01); *A61Q 1/10* (2013.01); *A61Q 15/00* (2013.01); *A61Q 17/04* (2013.01); *A61Q 19/10* (2013.01); *A61K 2800/10* (2013.01); *A61K 2800/59* (2013.01); *A61Q 1/06* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 4,526,780 A | 7/1985 | Marschner et al. | |
| 5,489,482 A * | 2/1996 | Minemura | ........... C09D 183/08 524/588 |
| 2006/0280712 A1 | 12/2006 | Kuroda et al. | |
| 2009/0053159 A1 | 2/2009 | Brun | |

(Continued)

FOREIGN PATENT DOCUMENTS

| | | |
|---|---|---|
| CN | 102438583 A | 5/2012 |
| EP | 0118625 A2 * | 9/1984 |

(Continued)

OTHER PUBLICATIONS

A Chemical Book web page https://www.chemicalbook.com/ChemicalProductProperty_EN_CB8307860.htm obtained on the internet (Year: 2017).*
English translation for EP0118625A2 (Year: 1984).*
Apr. 1, 2021 extended Search Report issued in European Patent Application No. 18844771.8.

(Continued)

*Primary Examiner* — Sin J Lee
(74) *Attorney, Agent, or Firm* — Oliff PLC

(57) ABSTRACT

A cosmetic including at least one cyclic silicone represented by formula (1), and having a boiling point of 205 to 255° C. and a viscosity of less than 5 mm²/s (25° C.). This cosmetic has a light touch, a good spread, and excellent water repellency, forms a uniform cosmetic film, can achieve a feeling of use without a strong oily feeling, and has stability over time and cosmetic persistence when a variety of oil such as a silicone, hydrocarbon oil, and ester, an organic ultraviolet absorber, or an oily component being solid at 25° C. is mixed.

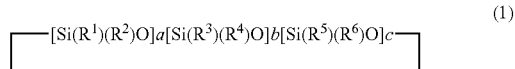

(1)

(Wherein $R^1$ is a monovalent hydrocarbon group having 2 or 3 carbon atoms, $R^2$, $R^3$, $R^4$, $R^5$, and $R^6$ are each independently a monovalent hydrocarbon group having 1 to 3 carbon atoms, "a" is a positive number satisfying $0<a<4$, and "b" and "c" are each independently a number of 0 to 3, provided that $(a+b+c) \leq 4$.)

12 Claims, No Drawings

(56) References Cited

U.S. PATENT DOCUMENTS

| | | |
|---|---|---|
| 2010/0158834 A1 | 6/2010 | Falk |
| 2012/0237583 A1 | 9/2012 | Hayashi et al. |
| 2021/0087461 A1 | 3/2021 | Huber |

FOREIGN PATENT DOCUMENTS

| | | |
|---|---|---|
| EP | 3 434 748 A1 | 1/2019 |
| GB | 659011 A | 10/1951 |
| JP | H07-179819 A | 7/1995 |
| JP | 3658561 B2 | 6/2005 |
| JP | 2006-019377 A | 1/2006 |
| JP | 2012-516286 A | 7/2012 |
| WO | 2010-080482 A2 | 7/2010 |

OTHER PUBLICATIONS

Feb. 11, 2020 International Preliminary Report on Patentability issued in International Patent Application No. PCT/JP2018/023822.
Jun. 9, 2020 Notification of Reasons for Refusal in Japanese Patent Application No. 2017-155287.
Aug. 14, 2018, International Search Report issued in International Patent Application No. PCT/JP2018/023822.
Nov. 9, 2021 issued in European Patent Application No. 18844771.8.
May 22, 2022 Office Action issued in Chinese Application No. 201880051988.0.

* cited by examiner

COSMETIC

TECHNICAL FIELD

The present invention relates a cosmetic containing a cyclic silicone.

BACKGROUND ART

A silicone typified by dimethylpolysiloxane has features such as a light touch, a good spread, excellent water repellency, and high safety, and therefore in recent years, the silicone has been often used as an oil used for the cosmetic.

For example, a cosmetic containing a volatile cyclic siloxane such as octamethyltetrasiloxane (D4), decamethylpentasiloxane (D5), or dodecamethylhexasiloxane (D6), a linear siloxane having a viscosity of 0.65 to 6 mm²/second at 25° C., or a volatile siloxane having a branched siloxane chain such as tristrimethylsiloxymethylsilane (M3T) has a light touch, a good spread, and excellent water repellency when the cosmetic is applied to the skin (Patent Document 1).

However, these silicones have problems in which the compatibility with a polar oil is poor and the silicones cannot be mixed as they remain clear, and therefore the feeling of use and stability of the cosmetic may be deteriorated. In particular, this trend is significantly represented when an organic ultraviolet absorber is used. When the silicones have low affinity for an oily component mixed for solidification of a cosmetic, such as a wax, crystallization of the oily component is prevented, and an expected hardness of a preparation cannot be obtained.

To solve the problems, that is, to enhance the compatibility with a polar oil, a wax, or the like, use of a phenyl-modified silicone, an ester, or the like as a compatibilizer is known. In this case, the feeling of use is poor, and a light touch of silicone may not be lost. Further, most of oil such as the phenyl-modified silicone and the ester has nonvolatility or does not have high volatility, and therefore an oily feeling may be strongly felt after application of a cosmetic to the skin.

To control the volatilization rate after application of a cosmetic, Patent Document 2 proposes a cosmetic composition containing a mixture of at least two types of cycloalkyl methicones having different volatilization rates as a technique using a cycloalkyl methicone for a cosmetic. However, Patent Document 2 does not disclose use of a cyclic silicone to improve the compatibility with a polar oil, a wax, and the like. Since the at least two types of cycloalkyl methicones having different volatilization rates are necessary, formulation design is also complicated.

Patent Document 3 discloses use of a silicone that is a composition of [—R₂SiO—]ₙ (wherein R is an alkyl group having 1 to 4 carbon atoms, and n is 3 to 10, and preferably 3 to 7) in an antiperspirant. However, a description about mixing compounds other than dimethylcyclo methicone is not found in Patent Document and use of a cyclic silicone to improve the compatibility with a polar oil, a wax, and the like is not disclosed in Patent Document 3. Further, Patent Document 3 does not disclose use of a cyclic silicone to achieve desired volatility and feeling of use.

CITATION LIST

Patent Literature

Patent Document Japanese Patent No. 3658561
Patent Document 2: WO2010/080482
Patent Document 3: U.S. Pat. No. 4,526,780

SUMMARY OF INVENTION

Technical Problem

In view of the above situation, it is an object of the present invention to provide a cosmetic which has a light touch, a good spread, and excellent water repellency, forms a uniform cosmetic film, can achieve a good feeling of use without strongly feeling an oily feeling, and has excellent stability over time and cosmetic persistence even when a variety of oil such as a silicone, a hydrocarbon oil, and an ester, an organic ultraviolet absorber, or an oily component being solid at 2.5° C. is mixed.

Solution to Problem

In order to solve the above-described problems, the present invention provides a cosmetic containing at least one cyclic silicone represented by the following general formula (1), and having a boiling point of 205 to 255° C. and a viscosity of less than 5 mm²/s (25° C.)

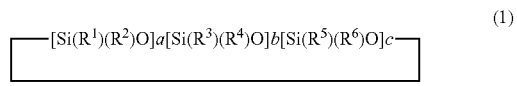

$$\mathrm{[Si(R^1)(R^2)O]}a\mathrm{[Si(R^3)(R^4)O]}b\mathrm{[Si(R^5)(R^6)O]}c \quad (1)$$

Wherein $R^1$ is a monovalent hydrocarbon group having 2 or 3 carbon atoms, $R^2$, $R^3$, $R^4$, $R^5$, and $R^6$ are each independently a monovalent hydrocarbon group having 1 to 3 carbon atoms, "a" is a positive number satisfying 0<a<4, and "b" and "c" are each independently a number of 0 to 3, provided that (a+b+c)≤4.

Such a cosmetic has a light touch, a good spread, and excellent water repellency, forms a uniform cosmetic film, and can achieve a good feeling of use without strongly feeling an oily feeling. Further, the cosmetic has excellent stability over time and cosmetic persistence even when an oil such as a silicone, a hydrocarbon oil, and an ester, an organic ultraviolet absorber, or an oily component being solid at 25° C. is mixed.

In this case, it is preferable that the cyclic silicone be selected from the group consisting of 1,3-dipropyl-1,3,5,5-tetramethylcyclotrisiloxane, 1,3,5-tripropyl-1,3,5-trimethylcyclotrisiloxane, 3,5,5-tetraethyl-1,3-dimethylcyclotrisiloxane, 1,3,3,5,5-pentaethyl-1-methylcyclotrisiloxane, 1,1,3,3,5,5-hexaethylcyclotrisiloxane, 1-propyl-1,3,3,5,5,7,7-heptamethylcyclotetrasiloxane, 1-ethyl-1,3,3,5,5,7,7-heptamethylcyclotetrasiloxane, 1,3-diethyl-1,3,5,5,7,7-hexamethylcyclotetrasiloxane, 1,3,5-triethyl-1,3,5,7,7-pentamethylcyclotetrasiloxane, and 1,3,5,7-tetraethyl-1,3,5,7-tetramethylcyclotetrasiloxane.

A cosmetic containing such a cyclic silicone can more assuredly achieve a good feeling of use without strongly feeling an oily feeling, and even when a variety of oil, an organic ultraviolet absorber, or an oily component being solid at 25° C. is mixed, the cosmetic has excellent stability over time and cosmetic persistence.

It is preferable that a cosmetic of the present invention further contain an organic ultraviolet absorber.

The cyclic silicone in the present invention has excellent compatibility with the organic ultraviolet absorber, and therefore a cosmetic containing such an organic ultraviolet absorber has a good feeling of use and excellent stability over time and cosmetic persistence.

In this case, it is preferable that the organic ultraviolet absorber be one or more types selected from ethylhexyl methoxycinnamate, diethylamine hydroxybenzoyl hexyl benzoate, octyl salicylate, polysilicone-15, t-butyl methoxydibenzoylmethane, oxybenzone, methylene bis-benzotriazolyl tetramethylbutylphenol, bis-ethyihexyloxy-phenol methoxyphenyl triazine, and octocrylene.

Such an organic ultraviolet absorber is preferable since the organic ultraviolet absorber has especially excellent compatibility with the cyclic silicone in the present invention.

It is preferable that the cosmetic of the present invention further contain an oily component being solid at 25° C.

The cyclic silicone in the present invention is preferable even during use in combination with the component being solid at 25° C. since a stick preparation or the like can be easily prepared without preventing solidification of the oily component due to high affinity of the cyclic silicone for the oily component.

In this case, it is preferable that the oily component being solid at 25° C. be one or more types selected from a polyethylene, ceresin, ozokerite, beeswax, microcrystalline wax, stearyl alcohol, behenyl alcohol, and cetanol.

Such an oily component is preferable since the oily component has especially high affinity for the cyclic silicone in the present invention.

Advantageous Effects of Invention

The cosmetic of the present invention includes the cyclic silicone represented by the general formula (1) as a base composition, and therefore the cosmetic has a light touch, a good spread, and excellent water repellency, forms a uniform cosmetic film, and further has excellent stability over time and cosmetic persistence even in a system where a variety of oil such as a silicone other than the cyclic silicone in the present invention used for the cosmetic, a hydrocarbon oil, and an ester, or the organic ultraviolet absorber is mixed. In addition, during use in combination with the oily component being solid at 25° C., a stick preparation or the like can be easily prepared without preventing solidification of the oily component. The cyclic silicone in the present invention has a boiling point of 205 to 255° C. and expresses volatility or higher volatility, and therefore an oily feeling is not strongly felt after application of the cosmetic to the skin. The cyclic silicone in the present invention has a viscosity of less than 5 mm$^2$/s (25° C.), a feeling of use is good without significantly feeling a sticky feeling. In the present invention, it is not necessary that the volatilization rate be exactly controlled by combination of a cyclic compound having high volatility with a cyclic compound having mild volatility. Specifically, when the cyclic compound in the present invention, that is, the cyclic silicone having a boiling point of 205 to 255° C. and represented by the general formula (1) is used alone, the above-described object is achieved.

DESCRIPTION OF EMBODIMENTS

The present inventor has intensively studied to achieve the above-described object, and as a result, found that when a cosmetic contains a cyclic silicone having a specific structure, a boiling point falling within a predetermined range, and a viscosity falling within a predetermined range, the cosmetic has a light touch, a good spread, and excellent water repellency, forms a uniform cosmetic film, can achieve a good feeling of use without strongly feeling an oily feeling, and has excellent stability over time and cosmetic persistence even when a variety of oil such as a silicone, a hydrocarbon oil, and an ester, an organic ultraviolet absorber, or an oily component being solid at 25° C. is mixed, and completed the present invention. Hereinafter, the present invention will be described in detail.

Specifically, the present invention is a cosmetic containing at least one cyclic silicone represented by the following general formula (1), and having a boiling point of 205 to 255° C. and a viscosity of less than 5 mm$^2$/s at 25° C.,

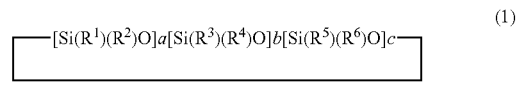

(1)

(wherein $R^1$ is a monovalent hydrocarbon group having 2 or 3 carbon atoms, $R^2$, $R^3$, $R^4$, $R^5$, and $R^6$ are each independently a monovalent hydrocarbon group having 1 to 3 carbon atoms, "a" is a positive number satisfying 0<a<4, and "b" and "c" are each independently a number of 0 to 3, provided that (a+b+c)≤4.)

In the above-described general formula (1), $R^1$ is a monovalent hydrocarbon group having 2 or 3 carbon atoms, and specific examples thereof include an ethyl group and a propyl group. $R^2$, $R^3$, $R^4$, $R^5$, and $R^6$ are each independently a monovalent hydrocarbon group having 1 to 3 carbon atoms, and specific examples thereof include a methyl group, an ethyl group, and a propyl group.

"a" is preferably 1 or 2, "b" and "c" are preferably 1 or 2, and (a+b+c) is preferably 3 or 4.

It is preferable that the general formula (1) satisfy that $R^1$ is the same as $R^2$, $R^3$ is the same as $R^4$, or $R^5$ is the same as $R^5$.

Since the cyclic silicone in the present invention has a boiling point of 205 to 255° C., the cyclic silicone has the same volatility as those of decamethylcyclopentasiloxane (boiling point: 210° C.) and dodecamethylcyclohexasiloxane (boiling point: 245° C.) Accordingly, an oily feeling is not strongly felt after application of the cosmetic to the skin. When the boiling point is lower than 205° C. it is difficult that the cosmetic is favorably applied and spread, and when it is higher than 255° C., an oily feeling is strongly felt.

Since the cyclic silicone in the present invention has a viscosity of less than 5 mm$^2$/s (25° C.), the cyclic silicone can be favorably applied and spread in the same manner as in a case of using decamethylcyclopentasiloxane having a viscosity of 4 mm$^2$/s (25° C.), or the like, and a feeling of use is good without significantly feeling a sticky feeling. When the viscosity is 5 mm$^2$/s (25° C.) or more, the spread is poor, a sticky feeling is produced, and a feeling of use is low.

It is preferable that the cyclic silicone in the present invention be especially selected from the group consisting of 1,3-dipropy-1,3,5,5-tetramethylcyclotrisiloxane, 1,3,5-tripropyl-1,3,5-trimethylcyclotrisiloxane, 1,3,5,5-tetraethyl-1,3-dimethylcyclotrisiloxane, 1,3,3,5,5-pentaethyl-1-methylcyclotrisiloxane, 1,1,3,3,5,5-hexaethylcyclotrisiloxane, 1-propyl-1,3,3,5,5,7,7-heptamethylcyclotetrasiloxane, 1-ethyl-1,3,3,5,5,7,7-heptamethylcyclotetrasiloxane, 1,3-diethyl-1,3,5,5,7,7-hexamethylcyclotetrasiloxane, 1,3,5-triethyl-1,3,5,7,7-pentamethylcyclotetrasiloxane, and 1,3,5,7-tetraethyl-1,3,5,7-tetramethylcyclotetrasiloxane.

Since the cyclic silicone in the present invention has excellent compatibility with a general-purpose component to be mixed in a variety of cosmetic, the cyclic silicone can be used in combination with any component. For a preparation in which a silicone having excellent compatibility with an organic ultraviolet absorber such as ethylhexyl methoxycinnamate and used to express a light feeling of use, a cosmetic having excellent stability over time and cosmetic persistence can be obtained.

During use in combination with an oily component being solid at 25° C., such as a polyethylene, ceresin, ozokerite, beeswax, microcrystalline wax, stearyl alcohol, behenyl alcohol, and cetanol, a stick preparation or the like can be easily prepared without preventing solidification of the oily component.

Therefore, when the cyclic silicone in the present invention is used, a cosmetic which has a light touch, a good spread, and excellent water repellency, forms a uniform cosmetic film, can achieve a good feeling of use without strongly feeling an oily feeling, and has excellent stability over time and cosmetic persistence even in a system where a variety of oil such as a silicone, a hydrocarbon oil, and an ester, and the organic ultraviolet absorber is mixed can be obtained and a stick preparation or the like can be easily prepared.

When as the cyclic silicone in the present invention, two or more types of cyclic silicone having different viscosities are used in combination, the feeling of use and the volatilization rate can be adjusted. To achieve a slow volatilization rate, the cyclic silicone can be used alone for a cosmetic without strict adjustment.

In the present invention, when an ultraviolet light shielding effect is desired for a cosmetic, it is preferable that an ultraviolet absorber be mixed.

The ultraviolet absorber is not particularly limited as long as it is a raw material capable of being usually mixed in the cosmetic. Specific examples thereof include homomenthyl salicylate, octocrylene, t-butyl methoxydibenzoylmethane, 4-(2-β-glucopyranosiloxylpropoxy-2-hydroxybenzophenone, octyl salicylate, diethylamino hydroxybenzoyl hexyl benzoate, oxybenzone-6, oxybenzone-9, oxybenzone-1, polysilicone-15, 1-(3,4-dimethoxyphenyl)-4,4-dimethyl-1,3-pentanedione, octyl dimethoxybenzylidene dioxoimidazolidine propionate, oxybenzone-2, terephthalylidene dicamphor sulfonic acid, 2,4,6-tris[4-(2-ethylhexyloxycarbonyl)anilino]-1,3,5-triazine, methylbis(trimethylsiloxy)silyl isopentyl trimethoxycinnamate, drometrizole trisiloxane, 2-ethylhexyl para-dimethylaminobenzoate, isopropyl para-methoxycinnamate, ethylhexyl methoxycinnamate, bis-ethylhexyloxyphenol methoxyphenyl triazine, oxybenzone-3, oxybenzone-4, oxybenzone-5, phenylbenzimidazole sulfonic acid, and methylene bis-benzotriazolyl tetramethylbutylphenol. Further, an UVA absorber (e.g, diethylamino hydroxybenzoyl hexyl benzoate) and an UVB absorber (e.g., ethylhexyl methoxycinnamate) can be used together, or in any combination.

Among these, one or more types of organic ultraviolet absorbers selected from ethylhexyl methoxycinnamate, diethylamino hydroxybenzoyl hexyl benzoate, octyl salicylate, polysilicone-15, t-butyl methoxydibenzoylmethane, oxybenzone, methylene bis-benzotriazolyl tetramethylbutylphenol, bis-ethylhexyloxyphenol methoxyphenyl triazine, and octocrylene are preferable since the compatibility thereof with the cyclic silicone in the present invention is excellent.

In the present invention, it is preferable that a wax, a hydrocarbon, an ester, a higher alcohol, or a higher fatty acid in a solid state at 25° C. be mixed for solidification of the cosmetic.

Examples of an oily component being solid at 25° C. include a wax, a hydrocarbon, an ester, a higher alcohol, and a higher fatty acid which have a melting point of preferably 40° C. or higher, and more preferably 60 to 110° C., and the oily component being solid at 25° C. is not particularly limited as long as it is a raw material capable of being usually mixed in the cosmetic. Specific examples thereof include a vegetable wax such as carnauba wax, candelilla wax, rice bran wax, and Japan wax, an animal wax such as beeswax and spermaceti, a hydrocarbon-based wax such as solid paraffin, a polyethylene, ceresin, ozokerite, and microcrystalline wax, a higher alcohol such as stearyl alcohol, behenyl alcohol, and cetanol, a fatty acid such as stearic acid and behenic acid, and a silicone wax such as an acrylic-silicone resin that is an acrylic-silicone graft or block copolymer (acrylic-silicone graft copolymer: KP-561P, 562P, or the like, available from Shin-Etsu Chemical Co., Ltd.) or a derivative Thereof, and one or more types selected from these are preferable.

In particular, the oily component being solid at 25° C. selected from a polyethylene, ceresin, ozokerite, beeswax, microcrystalline wax, stearyl alcohol, behenyl alcohol, and cetanol is preferable since the oily component has especially high affinity for the cyclic silicone in the present invention.

In the cosmetic of the present invention, a variety of optional component used for a general cosmetic can be mixed.

Other Optional Component

Another optional component may contain, for example, (1) an oil, (2) a compound having an alcoholic hydroxyl group, (3) a surfactant, (4) a powder, (5) a composition including a crosslinked organopolysiloxane and an oil in a liquid state at room temperature, (6) a film-forming agent, (7) an antiperspirant, (8) an antibacterial agent, and (9) another additive. One type of the other optional component may be used one or more types thereof may be used in combination as appropriate.

(1) Oil

The oil may be in a semisolid or liquid state except for the oily component being solid at 25° C. described above, and for example, natural animal and vegetable oil and fat and semisynthetic oil and fat, a hydrocarbon oil, a higher fatty acid, a higher alcohol, and an ester, a silicone oil other than the above-described cyclic silicone that is an essential component for expressing the effects of the present invention, or a fluorine-based oil can be used.

Natural Animal and Vegetable Oil and Fat and Semisynthetic Oil and Fat

Example of the natural animal and vegetable oil and fat and semisynthetic oil and fat include avocado oil, linseed oil, almond oil, Chinese wax, perilla oil, olive oil, cocoa butter, kapok wax, kaya oil, carnauba wax, cod liver oil, candelilla wax, purified candelilla wax, beef tallow, neat's foot oil, neat's hone fat, hardened beef tallow, apricot kernel oil, spermaceti, hydrogenated oil, wheat germ oil, sesame seed oil, fermented rice extract, rice bran oil, sugar cane wax, sasanqua oil, safflower oil, rhea butter, Chinese tung oil, cinnamon oil, jojoba wax, squalane, squalene, shellac wax, turtle oil, soybean oil, tea seed oil, camellia oil, evening primrose oil, corn oil, lard, rapeseed oil, Japanese Lung oil, rice bran wax, germ oil, horse fat, persic oil, palm oil, palm kernel oil, castor oil, hydrogenated castor oil, castor oil fatty acid methyl ester, sunflower oil, grape seed oil, bayberry wax, jojoba oil, macadamia seed oil, beeswax, mink oil, meadowfoam oil, cottonseed oil, cotton wax, Japan wax, Japan wax kernel oil, montan wax, palm oil, hydrogenated palm oil, tripalm oil fatty acid glyceride, mutton tallow, peanut oil, lanolin, liquid lanolin, reduced lanolin, lanolin alcohol, hard lanolin, acetylated lanolin, acetylated lanolin alcohol, lanolin fatty acid isopropyl, polyoxyethylene lanolin alcohol ether, polyoxyethylene lanolin alcohol acetate, lanolin fatty acid polyethylene glycol, polyoxyethylene hydrogenated lanolin alcohol ether, and egg yolk oil.

Hydrocarbon Oil

Examples of the hydrocarbon oil include a linear or branched hydrocarbon oil, and the hydrocarbon oil may be a volatile hydrocarbon oil or a nonvolatile hydrocarbon oil. Specific examples thereof include an α-olefin oligomer, light isoparaffin, isododecane, isohexadecane, light liquid isoparaffin, squalane, synthetic squalane, vegetable squalane, squalene, liquid paraffin, liquid isoparaffin, polyisobutylene, hydrogenated polyisobutene, and vaseline.

Higher Fatty Acid

Examples of the higher fatty acid include oleic acid, linoleic acid, linolenic acid, arachidonic acid, eicosapentaenoic acid (EPA), docosahexaenoic acid (DHA), isostearic acid, and 12-hydroxystearic acid.

Higher Alcohol

Examples of the higher alcohol include alcohols having preferably 6 or more carbon atoms. Specific examples of the higher alcohol include oleyl alcohol, isostearyl alcohol, 2-decyltetradecinol, cholesterol, phytosterol, polyoxyethylene cholesterol ether, monostearyl glyceryl ether (batyl alcohol), and monooleyl glyceryl ether (selachyl alcohol).

Ester

Examples of the ester include diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, isopropyl lauroylsarcosinate, diisostearyl malate, and the like; and glyceride oil such as acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

Silicone Oil

As the silicone oil, a silicone oil other than the cyclic silicone that is an essential component for expressing the effects of the present invention can be mixed. Examples of the silicone oil include linear or branched organopolysiloxanes having low to high viscosity such as dimethylpolysiloxane (KF-96L-1cs, KF-96L-1.5cs, KF-96L-2cs, and the like; available from Shin-Etsu Chemical Co., Ltd.), octamethyltetrasiloxane (D4), decamethylpentasiloxane (KF-995, available from Shin-Etsu Chemical Co., Ltd.), dodecamethylhexasiloxane (D6), tristrimethylsiloxymethylsilane (TMF-1.5 available from Shin-Etsu Chemical Co., Ltd.), caprylylmethicone, phenyl trimethicone, methylphenyl polysiloxane (KF-54 and KF-54HV, available from Shin-Etsu Chemical Co., Ltd.), diphenylsiloxyphenyl trimethicone (KF-56A available from Shin-Etsu Chemical Co., Ltd.), methylhexyl polysiloxane, methylhydrogenpolysiloxane, and a dimethylsiloxane-methylphenylsiloxane copolymer, a silicone rubber such as amino-modified organopolysiloxane, pyrrolidone-modified organopolysiloxane, pyrrolidone carboxylic acid-modified organopolysiloxane, gum-like dimethylpolysiloxane having a high degree of polymerization, gum-like amino-modified organopolysiloxane, and a gum-like dimethylsiloxane-methylphenylsiloxane copolymer, and a cyclic organopolysiloxane solution of silicone gum or rubber, amino acid-modified silicone, fluorine-modified silicone, a silicone resin, a dissolved product of silicone resin, and the like.

Fluorine-Based Oil

Examples of the fluorine-based oil include perfluoropolyether, perfluorodecalin, perfluorooctane, and the like.

(2) Compound Having Alcoholic Hydroxyl Group

Examples of the compound having an alcoholic hydroxyl group include lower alcohols preferably having 2 to 5 carbon atoms such as ethanol and isopropanol, and sugar alcohols such as sorbitol and maltose. Further examples thereof include sterols such as cholesterol, sitosterol, phytosterol, and lanosterol, and polyhydric alcohols such as butylene glycol, propylene glycol, dibutylene glycol, and pentylene glycol.

(3) Surfactant

The surfactant includes nonionic, anionic, cationic, and ampholytic activators, but is not particularly limited to these, and any surfactant may be used as long as it is used for a general cosmetic. Among these surfactants, a partially crosslinked polyether-modified silicone, a partially crosslinked polyglycerol-modified silicone, a linear or branched polyoxyethylene-modified organopolysiloxane, a linear or branched polyoxyethylene-polyoxypropylene-modified organopolysiloxane, a linear or branched polyoxyethylene/alkyl-co-modified organopolysiloxane, a linear or branched polyoxyethylene-polyoxypropylene/alkyl-co-modified organopolysiloxane, a linear or branched polyglycerol-modified organopolysiloxane and a linear or branched polyglycerol/alkyl-co-modified organopolysiloxane are preferable. In these surfactants, it is preferable that the content of hydrophilic polyoxyethylene group, polyoxyethylene-polyoxypropylene group, or polyglycerol residue be 10 to 70% by mass of the molecule. When the partially crosslinked polyether-modified silicone or the partially crosslinked polyglycerol-modified silicone is used, it is preferable that in a composition including the crosslinked organopolysiloxane and an oil in a liquid state at room temperature, the crosslinked organopolysiloxane contain the liquid oil in an amount of equal to or more than the weight of the crosslinked organopolysiloxane and be swollen relative to an liquid oil. The liquid oil may be the cyclic silicone in the present invention, or a liquid silicone oil, hydrocarbon oil, ester oil, natural animal or vegetable oil, semisynthetic oil, or fluorine-based oil in the oil (1) that is the optional component can be used. Examples of the liquid oil include a silicone oil having a low viscosity of 0.65 to 100 mm$^2$/s (25° C.), a hydrocarbon oil such as liquid paraffin, squalane, isododecane, and isohexadecane, a glyceride oil such as trioctanoin, an ester oil such as isotridecyl isononanoate, N-acyl glutamate, and lauroyl sarcosinate, and a natural animal or vegetable oil soon as macadamia seed oil. Specific examples thereof include KSG-210, 240, 310, 320, 330, 340, 320Z, 350Z, 710, 810, 820, 830, 840, 820Z, 850Z, and the like, available from Shin-Etsu Chemical Co., Ltd, Specific examples of a surfactant that is not the crosslinked organopolysiloxane include KF-6011, 6013, 6043, 6017, 6028, 6038, 6048, 6100, 6104, 6105, 6106, and the like available from Shin-Etsu Chemical Co., Ltd. Even in any case, the amount of the surfactant to be mixed is preferably 0.1 to 20% by mass relative to the whole cosmetic. When the amount is 0.1% by mass or more, a function such as dispersion and emulsification can be sufficiently achieved, and when it is 20% by mass or less, the cosmetic may not produce a sticky feeling of use. Therefore, this is preferable. HLB of the surfactant is not limited, and is preferably 2 to 14.5 in terms of maintaining the water resistance of the cosmetic.

(4) Powder

Examples of the powder include a color pigment, an inorganic powder, a metal powder, an organic powder, an inorganic-organic composite powder, and the like. Specific examples thereof are as follows.

Color Pigment

The color pigment is not particularly limited as long as it is a pigment usually used for colorization of the cosmetic, and red iron oxide, yellow iron oxide, white titanium oxide, black iron oxide, red oxide, ultramarine, iron blue, manganese violet, cobalt violet, chromium hydroxide, chromium oxide, cobalt oxide, cobalt titanate, iron oxide-doped titanium oxide, iron titanate, calcined titanium/titanium oxide, lithium cobalt titanate, cobalt titanate, titanium nitride, an inorganic brown pigment such as iron hydroxide and γ-iron oxide, an inorganic yellow pigment such as yellow ocher, a colored pigment such as a laked tar-based dye and a laked natural dye, or the like can be used. The pigment may have any shape such as a spherical shape, a nearly spherical shape, a rod-like shape, a spindle shape, a petaloid shape, a strip shape, and an amorphous shape, and the geometrical aspect of the pigment is not particularly limited as long as it can impart color to the cosmetic.

Inorganic Powder

Examples of the inorganic powder include fine particles made of zirconium oxide, zinc oxide, cerium oxide, magnesium oxide, barium sulfate, calcium sulfate, magnesium sulfate, calcium carbonate, magnesium carbonate, talc, cleavable talc, mica, kaolin, sericite, muscovite, synthetic mica, phlogopite, lepidolite, biotite, lithia mica, silicic acid, silicon dioxide, fumed silica, water-containing silicon dioxide, aluminum silicate, magnesium silicate, magnesium aluminum silicate, calcium silicate, barium silicate, strontium silicate, metal tungstate, hydroxyapatite, vermiculite, HIGILITE™, bentonite, montmorillonite, hectorite, zeolite, ceramics, calcium secondary phosphate, alumina, aluminum hydroxide, boron nitride, boron nitride, glass, and the like. Examples of an inorganic color pearl pigment include pearl pigments such as titanium oxide-coated mica, bismuth oxychloride, titanium oxide-coated bismuth oxychloride, titanium oxide-coated talc, fish scale guanine, and titanium oxide-coated color mica.

Metal Powder

Examples of the metal powder include metal fine particles made of aluminum, copper, stainless, silver, and the like.

Organic Powder

Examples of the organic powder include powder made of silicone, a polyamide, a polyacrylic acid-acrylic acid ester, a polyester, a polyethylene, a polypropylene, a polystyrene, a styrene-acrylic acid copolymer, a divinylbenzene-styrene copolymer, a polyurethane, a vinyl resin, an urea resin, a melamine resin, benzoguanamine, polymethylbenzoguanamine, tetrafluoroethylene, polymethyl methacrylate (e.g., polymethyl methacrylate), cellulose, silk, nylon, a phenol resin, an epoxy resin, a polycarbonate, and the like. In particular, examples of the silicone include silicone resin particles (specifically KMP-590, 591, and the like, available from Shin-Etsu Chemical Co., Ltd.) and silicone resin-coated silicone rubber powder (specifically KSP-100, 101, 102, 105, 300, 411, 441, and the like, available from Shin-Etsu Chemical Co., Ltd.). Examples thereof include a metal soap and the like, and specific examples thereof include powder made of zinc stearate, aluminum stearate, calcium stearate, magnesium stearate, zinc myristate, magnesium myristate, zinc cetyl phosphate, calcium cetyl phosphate, sodium zinc cetyl phosphate, and the like. Further, examples thereof include an organic dye and the like, and specific examples thereof include tar-based dyes such as Red No. 3, Red No. 104, Red No. 106, Red No. 201, Red No. 202, Red No. 204, Red No. 205, Red No, 220, Red No. 226, Red No, 227, Red No, 228, Red No, 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No, 3, Green No. 201, Green No. 204, Green. No. 205, Orange No. 201, Orange No. 203, Orange No. 204, Orange No. 206, and Orange No. 207, and a natural dye such as carminic acid, laccainic acid, carthamin, brazilin, and crocin.

Inorganic-Organic Composite Powder

Examples of the inorganic-organic composite powder include composite powder in which the surface of inorganic powder is coated with organic powder by a general method publicly known.

As the above-described powder, powder obtained by treating the surface of particles can be used. A surface treatment agent for the surface is preferably capable of imparting hydrophobicity from the viewpoint of water resistance of the cosmetic, and examples of the surface treatment agent capable of imparting hydrophobicity include, but are not particularly limited to, a silicone treatment agent, a wax, a paraffin, an organic fluorine compound including perfluoroalkyl, phosphate, and the like, a surfactant, amino acid such as N-acyl glutamic acid, and a metal soap such as aluminum stearate and magnesium myristate. The silicone treatment agent is more preferable, and examples thereof include silane such as capryisilane (AES-3083 available from Shin-Etsu Chemical Co., Ltd.) and trimethoxysilyl dimethicone, or a silylating agent, a silicone oil such as dimethyl silicone (KF-96 series available from. Shin-Etsu Chemical Co., Ltd.), methyl hydrogen type polysiloxane (KF-92P, KF-9901, and the like, available from Shin-Etsu Chemical Co., Ltd.), and branched silicone type silicone treatment agent (KF-9908, KF-9909, and the like, available from Shin-Etsu Chemical Co., Ltd.), acrylic-silicone (KP-574 and KP-541, available from Shin-Etsu Chemical Co., Ltd.), and the like. Further, the above-described surface-hydrophobizing treatment agent may be used alone or more types thereof may be used in combination. Specific examples of a surface-treated color pigment include KTP-09 series, and especially KTP-09W, 09R, 09Y, 09B, and the like, available from Shin-Etsu Chemical Co., Ltd.

(5) Composition Including Crosslinked Organopolysiloxane and Oil in Liquid State at Room Temperature In the composition including a crosslinked organopolysiloxane and an oil in a liquid state at room temperature, it is preferable that the crosslinked organopolysiloxane contain the liquid oil in an amount of equal to or more than the weight of the crosslinked organopolysiloxane and be swollen relative to a liquid oil. The liquid oil may be the cyclic silicone in the present invention, or a liquid silicone oil, hydrocarbon oil, ester oil, natural animal or vegetable oil, semisynthetic oil, or fluorine-based oil in the oil (1) that is the optional component can be used. Examples thereof include a silicone oil having a low viscosity of 0.65 to 100 $mm^2/s$ (25° C.), a hydrocarbon oil such as liquid paraffin, squalane, isododecane, and isohexadecane, a glyceride oil such as trioctanoin, an ester oil such as isotridecyl isononanoate, N-acyl ultimate, and lauroyl sarcosinate, and a natural animal or vegetable oil such as macadamia seed oil. The component (5) is a compound having no polyether or polyglycerol structure in the molecular structure, unlike the component (3) according to the present invention, and specific examples thereof include KSG series (trade name), and particularly KSG-15, 16, 016F, 19, 41, 42, 43, 44, 042Z, 045Z, and the like, available from Shin-Etsu Chemical Co., Ltd.

(6) Film-Forming Agent

The film-forming agent is mixed to further mainly maintain persistence of effect of the cosmetic. The film-forming agent is not particularly limited, and is preferably a silicone-based composition from the viewpoint of imparting water repellency. Specifically, trimethylsiloxy silicic acid, acrylic-silicone film-forming agent, silicone-modified norbornene, silicone-modified pullulan, or the like can be used. The film-forming agent may be mixed in the cosmetic after the film-forming agent is dissolved in the oil in a liquid state at room temperature. The liquid oil may be the cyclic silicone in the present invention, or a liquid silicone oil, hydrocarbon oil, ester oil, natural animal or vegetable oil, semisynthetic oil, or fluorine-based oil in the oil (1) that is the optional component can be used. Examples thereof include a silicone oil having a low viscosity of 0.65 to 100 $mm^2/s$ (25° C.), a hydrocarbon oil such as liquid paraffin, squalane, isododecane, and isohexadecane, a glyceride oil such as trioctanoin, an ester oil such as isotridecyl isononanoate, N-acyl glutamate, and lauroyl sarcosinate, and a natural animal or vegetable oil such as macadamia seed oil. Specific examples thereof include KF-7312J that is a product of trimethylsiloxy silicic acid dissolved in silicone, KP-545 and KP-549 that are a product of acrylic-silicone film-forming agent dissolved in silicone, NBN-30-ID that is a product of silicone-modified norbornene dissolved in isododecane, TSPL-30-ID that is a product of silicone-modified pullulan dissolved in isododecane, and TSPL-30-D5 that is a product dissolved in silicone, available from Shin-Etsu Chemical Co., Ltd., and the like.

(7) Antiperspirant

When the cosmetic according to the present invention is a deodorant, the antiperspirant can be optionally mixed. The antiperspirant is not particularly limited as long as it is a component that suppresses generation of sweat by constriction of the skin, and a general-purpose component can be widely used. Examples of the component include chlorohydroxy aluminum, aluminum chloride, aluminum chlorohydroxy allantoinate, aluminum allantoinate, tannic acid, potassium aluminum sulfate, zinc oxide, zinc para-phenolsulfonate, burnt alum, aluminum zirconium tetrachlorohydrate, aluminum zirconium trichlorohydrex glycine, and the like. In particular, a component expressing a high effect is preferably an adiaphoretic component selected from the group consisting of aluminum halide, aluminum hydroxyhalide, and a complex or mixture thereof with zirconyl oxyhalide and zirconyl hydroxyhalide. The antiperspirant that is mixed and dissolved in water or is mixed in a powder state in a preparation as it is can be used. As the antiperspirant, a commercially available product can be also used. The used commercially available product may be in a form of mixing a raw material with another component. The content of the antiperspirant is not particularly limited, and can appropriately vary depending on the amount of the other component to be mixed. In terms of obtaining a deodorant having excellent adiaphoretic effect as well as obtaining a deodorant having reduced stimulation against the skin, the content thereof preferably falls within a range of 0.001 to 30% by mass, and more preferably 0.01 to 20% by mass.

(8) Antibacterial Agent

The antibacterial agent is not particularly limited as long as it is a component in which a deodorization effect is obtained by suppressing proliferation of indigenous bacteria that produces a substance causing body odor on the skin. For example, an antibacterial drug such as triclosan, benzalkonium chloride, benzethonium chloride, chlorhexidine hydrochloride, chlorhexidine gluconate, halocarban, and isomethylphenol is generally used. Further, an antibacterial substance such as an essential oil or extract derived from a crude drug, including a green tea-dry-distilled extract and the like, may be mixed. As an antibacterial agent having a deodorization effect, such as an essential oil or extract derived from a crude drug, for example, green tea extract, lavender extract, scutellaria root extract, coptis rhizome extract, phellodendron bark extract, Artemisia capillaris extract, Aloe arborescens extract, Sophora flavescens root extract, rasa veitchii leaf extract, garlic extract, hamamelis extract, black tea extract, sage leaf extract, zanthoxylum extract, ginger root extract, calamus root extract, English ivy extract, houttuynia cordata extract, peach fruit extract, peach leaf extract, peppermint leaf extract, cnidium rhizome extract, eucalyptus leaf extract, peanut seed coat extract, litchi extract, burnet extract, or the like, can be used. One or more types of vegetable extracts may be mixed.

(9) Other Additive

Examples of the other additive include an oil-soluble gellant, an ultraviolet absorbing or scattering agent, a moisturizer, a preservative, a perfume, a salt, an antioxidant, a pH adjuster, a chelator, a refrigerant, an anti-inflammatory agent, a component for skin care (a skin-brightening agent, a cell activator, a rough skin-improving agent, a blood circulation promoter, a skin astringent, an antiseborrheic agent, etc.), vitamin, amino acid, nucleic acid, hormone, an inclusion compound, and the like.

Oil-Soluble Gellant

Examples of the oil-soluble gellant include a metal soap such as aluminum stearate, magnesium stearate and zinc myristate, an amino acid derivative such as N-lauroyl-L-glutamic acid and α,γ-di-n-butylamine, a dextrin fatty acid ester such as dextrin palmitate, dextrin stearate, and dextrin 2-ethylhexanoate palmitate, a sucrose fatty acid ester such as sucrose palmitate and sucrose stearate, a fructooligosaccharide fatty acid ester such as fructooligosaccharide stearate and fructooligosaccharide 2-ethylhexanoate, a benzylidene derivative of sorbitol such as monobenzylidene sorbitol and dibenzylidene sorbitol, an organically modified clay mineral such as dimethylbenzyldodecylammonium montmorillonite clay, dimethyldioctadecylammonium montmorillonite clay, and dimethyloctadecylammonium hectorite clay, and the like.

Ultraviolet Absorbing or Scattering Agent

Examples of the ultraviolet absorbing or scattering agent include fine particles that absorb or scatter ultraviolet light, such as titanium oxide fine particles, iron-containing titanium oxide fine particles, zinc oxide fine particles, cerium oxide fine particles, and composites thereof, and a dispersion in which the fine particles that absorb or scatter ultraviolet light are dispersed in an oil in advance can be used. The oil may be the cyclic silicone in the present invention, or a liquid silicone oil, hydrocarbon oil, ester oil, natural animal or vegetable oil, semisynthetic oil, or fluorine-based oil in the oil (1) that is the option-1 component can be used. Examples thereof include a silicone oil having a low viscosity of 0.65 to 100 $mm^2/s$ (25° C.), a hydrocarbon oil such as liquid paraffin, squalane, isododecane, and isohexadecane, a glyceride oil such as trioctanoin, an ester oil such as isotridecyl isononanoate, N-acyl glutamate, and lauroyl sarcosinate, and a natural animal or vegetable oil such as macadamia seed oil. Specific examples of the dispersion in which the fine particles that absorb or scatter ultraviolet light in the oil in advance include SPD series (trade name), and particularly SPD-T5, Z5, T6, Z6, and the like, available from Shin-Etsu Chemical Co., Ltd.

Moisturizer

Examples of the moisturizer include glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carbonylate, polyoxyethylene methyl glucoside, polyoxypropylene methyl glucoside, egg-yolk lecithin, soybean lecithin, phosphatidylcholine, phosphatidylethanolamine, phosphatidylserine, phosphatidylglycerol, phosphatidylinositol, sphingophospholipid, and the like.

Preservative

Examples of the preservative include alkyl para-hydroxybenzoate, benzoic acid, sodium benzoate, sorbic acid, potassium sorbate, phenoxyethanol, and the like, and examples of the an agent include benzoic acid, salicylic acid, phenol, sorbic acid, alkyl para-hydroxybenzoate, para-chloro-meta-cresol, hexachlorophene, trichlorocarbanilide, a photosensitizer, phenoxyethanol, and the like.

Perfume

The perfume include a natural perfume and synthetic perfume. Examples of the natural perfume include a vegetable perfume obtained by separating from a flower, a leaf, a material, a peel, and the like; and an animal perfume such as musk and civet. Examples of the synthetic perfume include a hydrocarbon such as monoterpene, an alcohol such as an aliphatic alcohol and an aromatic alcohol; an aldehyde such as terpene aldehyde and aromatic aldehyde; a ketone such as alicyclic ketone; an ester such as a terpene-based ester; a lactone; a phenol; an oxide; a nitrogen-containing compound; an acetal; and the like.

Salt

Examples of the salt include an inorganic salt, an organic acid salt, an amine salt, and an amine acid salt. Examples of the inorganic salt include a sodium salt, a potassium salt, a magnesium salt, a calcium salt, an aluminum salt, a zirconium salt, and a zinc salt, and the like of inorganic acid such as hydrochloric acid, sulfuric acid, carbonic acid, and nitric acid; examples of the organic acid salt include a salt of organic acid such as acetic acid, dehydroacetic acid, citric acid, malic acid, succinic acid, ascorbic acid, and stearic acid; and examples of the amine salt and the amino acid salt include a salt of amine such as triethanolamine, and a salt of amino acid such as glutamic acid. In addition, a salt of hyaluronic acid, chondroitin sulfate, or the like, aluminum zirconium glycine complex, an acid-alkali neutralizing salt used in preparation of the cosmetic, or the like can be used.

Antioxidant

Examples of the antioxidant include, but are particularly limited to, carotenoid, ascorbic acid and a salt thereof, ascorbyl stearate, tocophenol, tocophenol acetate, tocopherol, p-t-butylphenol, butylhydroxyanisol, dibutylhydroxytoluene, phytic acid, ferulic acid, thiotaurine, hypotaurine, sulfite, erythorbic acid and a salt thereof, chlorogenic acid, epicatechin, epigallocatechin, epigallocatechin gallate, apigenin, campherol, myricetin, quercetin, and the like. One type of the antioxidant may be used alone or more types thereof may be used in combination.

pH Adjuster

Examples of the pH adjuster include lactic acid, citric acid, glycolic acid, succinic acid, tartaric acid, dl-malic acid, potassium carbonate, sodium bicarbonate, ammonium bicarbonate, and the like.

Chelator

Examples of the chelator include alanine, sodium edetate, sodium polyphosphate, sodium metaphosphate, phosphoric acid, and the like.

Refrigerant

Examples of the refrigerant include L-menthol, camphor, and the like.

Anti-Inflammatory Agent

Examples of the anti-inflammatory agent include allantoin, glycyrrhizinic acid and a salt thereof, glycyrrhetinic acid and stearyl glycyrrhetinate, tranexamic acid, azulene, and the like.

Component for Skin Care

Examples of the component for skin care include a skin-brightening agent such as a placenta extract, arbutin, glutathione, and strawberry geranium extract, a cell activator such as royal jelly, a photosensitizer, a cholesterol derivative, and a calf blood extract; a rough skin-improving agent, a blood circulation promoter such as vanillylamide nonylate, benzyl nicotinate, β-butoxyethyl nicotinate, capsaicin, zingerone, cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthine, and γ-orizanol, a skin astringent such as zinc oxide and tannic acid, an antiseborrheic agent such as sulfur and thianthrol, and the like.

Vitamin

Examples of the vitamin include vitamin A such as vitamin A oil, retinol, retinol acetate, and retinol palmitate, vitamin B including vitamin $B_2$ such as riboflavin, riboflavin butyrate, and flavin adenine nucleotide, vitamin $B_6$ such as pyridoxine hydrochloride, pyridoxine dioctanoate, and pyridoxine tripalmitate, vitamin $B_{12}$ and a derivative thereof, and vitamin $B_{15}$ and a derivative thereof, vitamin C such as L-ascorbic acid, L-ascorbic acid dipalmitate, sodium L-ascorbic acid-2-sulfate, and dipotassium L-ascorbic acid diphosphate, vitamin D such as ergocalciferol and cholecalciferol, vitamin E such as α-tocopherol, β-tocopherol, γ-tocopherol, dl-α-tocopherol acetate, dl-α-tocopherol nicotinate, and dl-α-tocopherol succinate; nicotinic acid such as nicotinic acid, benzyl nicotinate, and amide nicotinate, pantothenic acid such as vitamin H, vitamin P, calcium pantothenate, D-pantothenyl alcohol, pantothenyl ethyl ether, and acetyl pantothenyl ethyl ether, biotin, and the like.

Amino Acid

Examples of the amino acid include glycine, valine, leucine, isoleucine, serine, threonine, phenylalanine, arginine, lysine, aspartic acid, glutamic acid, cystine, cysteine, methionine, tryptophan, and the like.

Nucleic Acid

Examples of the nucleic acid include deoxyribonucleic acid, and the like.

Hormone

Examples of the hormone include estradiol, ethenyl estradiol, and the like.

Inclusion Compound

Examples of the inclusion compound include cyclodextrin, and the like.

Examples of form of the cosmetic according to the present invention include powder, liquid, solid, and the like. The form of a preparation mainly include liquid, cream, aerosol, ointment, emulsified solid, stick, and emulsified stick.

EXAMPLES

A cyclic silicone (cycloalkylsiloxane) used in a cosmetic of the present invention was produced as follows. The viscosity is a viscosity measured at 25° C. with an Ostwald viscometer.

(Production Example 1) Synthesis of 1,3,5,7-Tetraethyl-1,3,5,7-tetramethylcyclotetrasiloxane 241 g (1.0 mol) of 1,3,5,7-tetramethylcyclotetrasiloxane and 2.4 mg of chloroplatinic acid were placed in a 1-L four-necked flask. An ethylene gas was blown into the mixture, and a reaction was caused while the temperature was held at 50 to 60° C. The reaction was monitored by gas chromatography. At a time point when the ratio of a target reached 90% or more, the reaction was terminated, and distillation under reduced pressure (120° C., 10 mmHg) was performed to obtain 1,3,5,7-tetraethyl-1,3,5,7-tetramethylcyclotetrasiloxane as the target. The boiling point was 245° C. and the viscosity was 4.5 $mm^2/s$.

(Production Example 2) Synthesis of 1-Ethyl-1,3,3,5,5,7,7-heptamethylcyclotetrasiloxane 1-ethyl-1,3,3,5,5,7,7-heptamethylcyclotetrasiloxane was obtained as a target in the same manner as in Production Example 1 except that 1,3,3,5,5,7,7-heptamethylcyclotetrasiloxane was used as a siloxane raw material. The boiling point was 210° C. and the viscosity was 2.9 $mm^2/s$.

(Production Example 3) Synthesis of 1-Propyl-1,3,3,5,5,7,7-heptamethylcyclotetrasiloxane 1-propyl-1,3,3,5,5,7,7-heptamethylcyclotetrasiloxane was obtained as a target in the same manner as in Production Example 1 except that 1,3,3,5,5,7,7-heptamethylcyclotetrasiloxane was used as a siloxane raw material and a propylene gas was blown as an unsaturated hydrocarbon raw material. The boiling point was 220° C. and the viscosity was 3.3 $mm^2/s$.

Solubility Test of Ethylhexyl Methoxycinnamate

The solubility between the cycloalkylsiloxanes obtained in Production Examples 1, 2, and 3 and an organic ultraviolet absorber was evaluated by a method described below. The evaluation results are shown in Table 1.

Evaluation Method

Ethylhexyl methoxycinnamate (sometimes referred to as OMC) and each silicone (sometimes referred to as Sx) were weighed at a mass ratio shown in Table 1, and shaken and mixed at room temperature for 24 hours, and the dissolution state after 12 days at room temperature was observed. The results are shown in Table 1.

For the dissolution state, dissolution is represented by good, and separation is represented by poor.

TABLE 1

| Silicone | Ratio of OMC:Sx | Dissolution state |
|---|---|---|
| KF-96L-1cs | 1:1 | poor |
| KF-96L-1.5cs | 1:1 | poor |
| KF-96L-2cs | 1:1 | poor |
| TMF-1.5 | 1:1 | poor |
| D5:KF-995 | 1:1 | poor |
| D6 | 1:1 | poor |
| Sx in Production Example 1 | 1:1 | good |
| Sx in Production Example 1 | 4:6 | good |
| Sx in Production Example 2 | 1:1 | good |
| Sx in Production Example 2 | 4:6 | good |

TABLE 1-continued

| Silicone | Ratio of OMC:Sx | Dissolution state |
|---|---|---|
| Sx in Production Example 3 | 1:1 | good |
| Sx in Production Example 3 | 4:6 | good |

As shown in Table 1, it was obvious that the cycloalkylsiloxanes obtained in Production Examples 1, 2 and 3 in the present invention dissolved ethylhexyl methoxycinnamate more than octamethyltrisiloxane (KF-96L-1cs available from Shin-Etsu Chemical Co., Ltd.), decamethyltetrasiloxane (KF-96L-1.5cs available from Shin-Etsu Chemical Co., Ltd.), undecamethylpentasiloxane (KF-96L-2cs available from Shin-Etsu Chemical Co., Ltd.), tristrimethylsiloxymethylsilane (TMF-1.5 available from Shin-Etsu Chemical Co., Ltd.), decamethylpentasiloxane (KF-995 available from Shin-Etsu Chemical Co., Ltd.), and dodecamethylhexasiloxane (D6).

Crystallization Test of Solid Oily Component at 25° C.

Influence of the cycloalkylsiloxanes obtained in Production Examples 1, 2, and 3 on crystallization of an oily component being solid at 25° C. was evaluated by a method described below. The evaluation results are shown in Table 2.

Evaluation Method

Each oily component being solid at 25° C. and each silicone were weighed at a mass ratio of 9:1, and heated and dissolved at 105° C. for 20 minutes. After then, the resultant was allowed to stand at 25° C. for 2 days, and the hardness of the solid material was measured with a rheometer.

Rheometer measurement condition: An automatic consistency measurement tester RPM-101 (manufactured by RIGOSHA) was used, a ¼ cone was set, and a penetration hardness after 5 seconds was measured. During penetration, the presence or absence of exudation of oil (: silicone) from a surface of the solid material was observed. The hardness is expressed by a numeric value. A higher value means that the solid material is hard. The absence of exudation is represented by good, and the presence of exudation is represented by poor.

TABLE 2

| Solid oily component | KF-96L-1.5cs | KF-96L-2cs | TMF-1.5 | D5 | D6 | Sx in Production Example 1 | Sx in Production Example 2 | Sx in Production Example 3 |
|---|---|---|---|---|---|---|---|---|
| Polyethylene | 34.4 | 73.5 | 46.3 | 66.9 | 59.5 | 44.6 | 48.9 | 45.1 |
| | good | poor | good | good | good | good | good | good |
| Ceresin | 42.9 | 45.7 | 23.5 | 66.7 | 40.7 | 84.4 | 78.4 | 73.1 |
| | good | good | good | good | good | good | good | good |
| Stearyl Alcohol | 55.4 | 38.0 | 54.5 | 32.9 | 43.0 | 33.5 | 36.3 | 31.2 |
| | good | good | good | good | good | good | good | good |
| Behenyl Alcohol | 73.3 | 59.6 | 50.0 | 55.9 | 56.5 | 63.5 | 58.6 | 61.1 |
| | poor | poor | poor | poor | poor | good | good | good |
| Cetanol | 5.25 | 49.1 | 53.1 | 53.3 | 46.4 | 35.9 | 40.2 | 38.4 |
| | poor | poor | poor | poor | poor | good | good | good |

As shown in Table 2, for the cycloalkylsiloxane in the present invention, oil did not exude during measurement even using any solid oily component, and it was obvious that solidification of the oily component was not prevented. In particular, when ceresin or behenyl alcohol was used, relatively high hardness was shown, and it was obvious that solidification was good.

Hereinafter, the present invention will be specifically described with reference to formulation examples of a cosmetic in Examples and Comparative Examples, and the present invention is not limited to these Examples. Unless otherwise specified, a mixing amount is represented in terms of % (% by mass).

(Examples 1 to 3 and Comparative Examples 1 to 5) W/O Type Foundation

In Examples 1 to 3, a WO type foundation was produced using the cycloalkylsiloxane obtained in Production Example 1 or 2 by the following production method, and in Comparative Examples 1 to 5, a W/O type foundation was produced without these cycloalkylsiloxanes by the following production method. Compositions in Examples 1 to 3 and Comparative Examples 1 to 5 are shown in Table 3.

TABLE 3

| | Example 1 | Example 2 | Example 3 | Comparative Example 1 | Comparative Example 2 | Comparative Example 3 | Comparative Example 4 | Comparative Example 5 |
|---|---|---|---|---|---|---|---|---|
| 1 Sx in Production Example 1 | 37.5 | — | 8.0 | — | — | — | — | — |
| 2 Sx in Production Example 2 | — | 37.5 | — | — | — | — | — | — |
| 3 Methyl trimethicone (note 1) | — | — | — | 37.5 | — | — | — | — |
| 4 Decamethylcyclopentasiloxane (note 2) | — | — | 29.5 | — | 37.5 | — | — | 29.5 |
| 5 Dodecamethylcyclohexasiloxane | — | — | — | — | — | 37.5 | — | — |
| 6 Dimethylsiloxyphenyl trimethicone (note 3) | — | — | — | — | — | — | 37.5 | 8.0 |
| 7 Ethylhexyl methoxycinnamate | 7.5 | 7.5 | 7.5 | 7.5 | 7.5 | 7.5 | 7.5 | 7.5 |
| 8 Crosslinked POE-modified silicone (note 4) | 3.5 | 3.5 | 3.5 | 3.5 | 3.5 | 3.5 | 3.5 | 3.5 |
| 9 Crosslinked dimethylpolysiloxane mixture (note 5) | 5.0 | 5.0 | 5.0 | 5.0 | 5.0 | 5.0 | 5.0 | 5.0 |
| 10 Silicone-branched POE-modified silicone (note 6) | 2.0 | 2.0 | 2.0 | 2.0 | 2.0 | 2.0 | 2.0 | 2.0 |
| 11 Disteardimonium hectorite | 1.2 | 1.2 | 1.2 | 1.2 | 1.2 | 1.2 | 1.2 | 1.2 |
| 12 Silicone-modified acrylic polymer (note 7) | 0.3 | 0.3 | 0.3 | 0.3 | 0.3 | 0.3 | 0.3 | 0.3 |
| 13 Silicone-treated titanium oxide (note 8) | 8.0 | 8.0 | 8.0 | 8.0 | 8.0 | 8.0 | 8.0 | 8.0 |
| 14 Silicone-treated red iron oxide (note 8) | 1.6 | 1.6 | 1.6 | 1.6 | 1.6 | 1.6 | 1.6 | 1.6 |
| 15 Silicone-treated yellow iron oxide (note 8) | 0.7 | 0.7 | 0.7 | 0.7 | 0.7 | 0.7 | 0.7 | 0.7 |
| 16 Silicone-treated black iron oxide (note 8) | 0.2 | 0.2 | 0.2 | 0.2 | 0.2 | 0.2 | 0.2 | 0.2 |
| 17 Dipropylene glycol | 5.0 | 5.0 | 5.0 | 5.0 | 5.0 | 5.0 | 5.0 | 5.0 |
| 18 Methyl para-hydroxybenzoate | 0.3 | 0.3 | 0.3 | 0.3 | 0.3 | 0.3 | 0.3 | 0.3 |
| 19 Sodium citrate | 0.2 | 0.2 | 0.2 | 0.2 | 0.2 | 0.2 | 0.2 | 0.2 |
| 20 Sodium chloride | 0.5 | 0.5 | 0.5 | 0.5 | 0.5 | 0.5 | 0.5 | 0.5 |
| 21 Ethanol | 3.0 | 3.0 | 3.0 | 3.0 | 3.0 | 3.0 | 3.0 | 3.0 |
| 22 Purified water | 23.5 | 23.5 | 23.5 | 23.5 | 23.5 | 23.5 | 23.5 | 23.5 |
| Total | 100.0 | 100. | 100.0 | 100.0 | 100.0 | 100. | 100.0 | 100.0 |

(note 1)
TMF-1.5 available from Shin-Etsu Chemical Co., Ltd.
(note 2)
KF-995 available from Shin-Etsu Chemical Co., Ltd.
(note 3)
KF-56A available from Shin-Etsu Chemical Co., Ltd.
(note 4)
KSG-210 available from Shin-Etsu Chemical Co., Ltd. (Mixture of 80% of dimethylpolysiloxane and 20% of POE-crosslinked silicone elastomer)
(note 5)
KSG-15 available from Shin-Etsu Chemical Co., Ltd. (Mixture of 93% of decamethylcyclopentasiloxane and 7% of silicone elastomer)
(note 6)
KF-6028P available from Shin-Etsu Chemical Co., Ltd.
(note 7)
KP-578 available from. Shin-Etsu Chemical Co., Ltd.
(note 8)
KTP-09W, R, Y, B available from Shin-Etsu Chemical Co., Ltd. (KF-9909 treatment color inorganic pigment, W: white, R: red, Y: yellow, B: black)

Production Method

A part of components 1 to 6, and components 7 to 11 were stirred and uniformly mixed. To the mixture, components 17 to 21 that had been uniformly dissolved in a component 22 separately was quietly added and stirred to obtain an emulsified product. Separately, a balance of the components 1 to 6 and components 12 to 16 were subjected to a roller treatment, and mixed in the emulsified product. The mixture was placed in a predetermined container, to obtain a foundation.

For (1) a good touch (light touch) (2) a good spread, (3) good uniformity of a film, and (4) good cosmetic persistence of the obtained W/O type foundations, a use test was performed by ten female experts, and evaluation was performed in accordance with the following evaluation criteria. Further, (5) a state after a cosmetic was left to stand at 40° C. for one month was observed. The evaluation results in Examples 1 to 3 and Comparative Examples 1 to 5 were shown in Table 4.

Evaluation Criteria 5 points: Very good
4 points: Good
3 points: Fair
2 points: Slightly poor
1 point: Poor An obtained average was decided accordance with the following criteria.

Decision of Average

The obtained average is 4.5 points or more: A
The obtained average is 3.5 points or more and less than 4.5 points: B
The obtained average is 2.5 points or more and less than 3.5 points: C
The obtained average is 1.5 points or more and less than 2.5 points: D
The obtained average is less than 1.5 points: E

TABLE 4

| No. | Evaluation item | Example 1 | Example 2 | Example 3 | Comparative Example 1 | Comparative Example 2 | Comparative Example 3 | Comparative Example 4 | Comparative Example 5 |
|---|---|---|---|---|---|---|---|---|---|
| (1) | Good touch | B | A | B | B | B | C | D | C |
| (2) | Good spread | A | A | A | B | A | B | A | A |
| (3) | Good uniformity of film | A | A | A | D | A | D | B | B |
| (4) | Good make-up durability | B | A | B | C | B | C | C | B |
| (5) | State of cosmetic material | Stable | Stable | Stable | Separation | Separation | Separation | Stable | Thickening |

As obvious from Table 4, a light touch was exhibited and a uniform film was obtained from the foundations in Examples 1 to 3 as compared with Comparative Examples 1 to 5, and it was demonstrated that the foundations had good make-up durability. Further, it was obvious that the foundations had excellent storage stability.

(Example 4) Sunscreen Emulsion (Shaking)

In accordance with formulation shown in Table 5, a sunscreen emulsion (shaking) was prepared.

TABLE 5

| | Component | Example 4 |
|---|---|---|
| 1 | Decamethylcyclopentasiloxane | 22.5 |
| 2 | Sx in Production Example 1 | 9.0 |

TABLE 5-continued

| | Component | Example 4 |
|---|---|---|
| 3 | Crosslinked dimethylphenylpolysiloxane (note 1) | 3.0 |
| 4 | Alkyl polyether-co-modified silicone (note 2) | 2.0 |
| 5 | Ethylhexyl methoxycinnamate | 7.5 |
| 6 | Hexyl diethylaminohydroxybenzoylbenzoate | 1.0 |
| 7 | Octocrylene | 2.5 |
| 8 | Disteardimonium hectorite | 1.0 |
| 9 | Acrylic-silicone resin dissolved product (note 3) | 2.0 |
| 10 | Spherical silicone resin composite powder (note 4) | 0.5 |
| 11 | Titanium oxide dispersion (note 5) | 5.0 |
| 12 | Zinc oxide dispersion (note 6) | 10.0 |
| 13 | 1,3-butylene glycol | 3.0 |
| 14 | Sodium citrate | 0.2 |
| 15 | Sodium chloride | 0.5 |
| 16 | Ethanol | 5.0 |
| 17 | Purified water | 25.3 |
| | Total | 100.0 |

(note 1)
KSG-18A available from Shin-Etsu Chemical Co., Ltd. (Mixture of 85% of diphenylsiloxy phenyl trimethicone and 15% of phenyl-modified crosslinked silicone elastomer)
(note 2)

TABLE 5-continued

| Component | Example 4 |
|---|---|

KF-6038 available from Shin-Etsu Chemical Co., Ltd.
(note 3)
KP-545 available from Shin-Etsu Chemical Co., Ltd. (Dissolved product of 70% of decamethylcyclopentasiloxane and 30% of acrylic- silicone)
(note 4)
KSP-105 available from Shin-Etsu Chemical Co., Ltd. (Composite powder including a silicone rubber coated with a silicone resin and having an average particle diameter of 2 μm)
(note 5)
SPD-T5 available from Shin-Etsu Chemical Co., Ltd. (Dispersion of 40% of titanium oxide fine particles in decamethylcyclopentasiloxane)
(note 6)
SPD-Z5 available from Shin-Etsu Chemical Co., Ltd. (Dispersion of 60% of zinc oxide fine particles in decamethylcyclopentasiloxane)

Production Method

A: Components 1 to 9 were uniformly mixed.
B: To A, a component 10 was added and uniformly dispersed.

C: In a component 17, components 13 to 16 were dissolved.
D: To C, B was gradually added and emulsified, and components 11 and 12 were then added to obtain a sunscreen emulsion.

It was found that the sunscreen emulsion obtained as described above had light spread and extension, exhibited a dry touch, did not exhibit stickiness, did not vary depending on temperature or time, and had very excellent usability and stability.

(Example 5) Sunscreen Cream

In accordance with formulation shown in Table 6, a

TABLE 6

|   | Component | Example 5 |
|---|---|---|
| 1 | Sx in Production Example 3 | 30.0 |
| 2 | Squalane | 3.0 |
| 3 | Silicone-branched alkyl polyglycerol-co-modified silicone (note 1) | 4.0 |
| 4 | Ethylhexyl methoxycinnamate | 7.5 |
| 5 | t-butylmethoxydibenzoylmethane | 3.0 |
| 6 | Polysilicone-15 | 1.0 |
| 7 | Distearyldimethylammonium chloride | 1.0 |
| 8 | Vitamin E acetate | 0.1 |
| 9 | Ethanol | 1.0 |
| 10 | Sodium citrate | 0.5 |
| 11 | Magnesium sulfate | 0.5 |
| 12 | Preservative | 0.3 |
| 13 | Purified water | 48.1 |
|   | Total | 100.0 |

(note 1)
KF-6105 available from Shin-Etsu Chemical Co., Ltd.

Production Method

A: Components 1 to 8 were uniformly mixed.
B: In a component 13, components 9 to 12 were uniformly dissolved.
C: To A, B was gradually added with stirring, and emulsified, to obtain a sunscreen cream.

It was found that the sunscreen cream obtained as described above had fine texture, had light spread and extension, gave wet and fresh feeling, did not attach sand at all due to the absence of stickiness, and had very good usability. Further, it was found that the sunscreen cream did not vary depending on temperature or time and had excellent stability.

(Example 6) Sunscreen Cream

In accordance with formulation shown in Table 7, a sunscreen cream was prepared.

TABLE 7

|   | Component | Example 6 |
|---|---|---|
| 1 | Sx in Production Example 2 | 16.0 |
| 2 | Crosslinked alkyl polyether-co-modified silicone (note 1) | 3.5 |
| 3 | Crosslinked dimethylphenylpolysiloxane (note 2) | 3.0 |
| 4 | Alkyl polyether-co-modified silicone (note 3) | 1.5 |

TABLE 7-continued

|   | Component | Example 6 |
|---|---|---|
| 5 | Trimethylsiloxy silicate dissolved product (note 4) | 3.0 |
| 6 | Ethylhexyl methoxycinnamate | 7.5 |
| 7 | t-butylmethoxydibenzoylmethane | 3.0 |
| 8 | Octyl salicylate | 3.0 |
| 9 | 1,3-butylene glycol | 5.0 |
| 10 | Sodium citrate | 0.5 |
| 11 | Sodium chloride | 1.0 |
| 12 | Preservative | 0.3 |
| 13 | Purified water | 52.7 |
|   | Total | 100.0 |

(note 1)
KSG-310 available from Shin-Etsu Chemical Co., Ltd. (Mixture of 70% of mineral oil and 30% of alkyl-modified POE-crosslinked silicone elastomer)
(note 2)
KSG-18A available from Shin-Etsu Chemical Co., Ltd. (Mixture of 85% of diphenylsiloxy phenyl trimethicone and 15% of phenyl-modified crosslinked silicone elastomer)
(note 3)
KF-6048 available from Shin-Etsu Chemical Co., Ltd.
(note 4)
KF-7312J available from Shin-Etsu Chemical Co., Ltd. (Dissolved product of 50% of decamethylcyclopentasiloxane and 50% of silicone resin)

Production Method

A: Components 1 to 8 were uniformly mixed.
B: In a component 13, components 9 to 12 were uniformly dissolved.
C: To A, B was gradually added with stirring, and emulsified, to obtain a sunscreen cream.

The sunscreen cream obtained as described above had light spread and extension, exhibited freshness and no stickiness, and had good make-up durability, and therefore an effect of preventing ultraviolet light was also sustained. Further, it was found that the sunscreen cream did not vary depending on temperature or time and had very excellent usability and stability.

(Example 7) Nonaqueous Mousse Foundation

In accordance with formulation shown in Table 8, a nonaqueous mousse foundation was prepared.

TABLE 8

|   | Component | Example 7 |
|---|---|---|
| 1 | Crosslinked polyether-modified silicone (note 1) | 18.0 |
| 2 | Dimethyl polysiloxane 6 mm$^2$/s | 1.0 |
| 3 | Sx in Production Example 1 | 11.0 |
| 4 | Ethylhexyl methoxycinnamate | 5.0 |
| 5 | Jojoba oil | 1.0 |
| 6 | Silylation treated silicic anhydride (note 2) | 0.75 |
| 7 | Silicone-treated red iron oxide (note 3) | 0.2 |
| 8 | Silicone-treated yellow iron oxide (note 3) | 1.0 |

TABLE 8-continued

| | Component | Example 7 |
|---|---|---|
| 9 | Silicone-treated black iron oxide (note 3) | 0.02 |
| 10 | Silicone-treated titanium oxide (note 3) | 5.0 |
| 11 | Silicone-treated talc | 11.55 |
| 12 | Trimethylsiloxy silicate dissolved product (note 4) | 4.0 |
| 13 | Decamethylcyclopentasiloxane | 25.28 |
| 14 | Spherical silicone resin composite powder (note 5) | 6.0 |
| 15 | Spherical polymethylsilsesquioxane powder (note 6) | 3.0 |
| 16 | Spherical alkyl polymethacrylate | 7.0 |
| 17 | Antioxidant | 0.2 |
| | Total | 100.0 |

(note 1)
KSG-240 available from Shin-Etsu Chemical Co., Ltd. (Mixture of 80% of decamethylcyclopentasiloxane and 20% of POE crosslinked silicone elastomer)
(note 2)
surface-hydrophobized fumed silica: AEROSIL R-972 available from Nippon Aerosil Co., Ltd.
(note 3)
KTP-09W, R, Y, B available from Shin-Etsu Chemical Co., Ltd. (KF-9909 treatment color inorganic pigment, W: white, R: red, Y: yellow, B: black)
(note 4)
KF-7312J available from Shin-Etsu Chemical Co., Ltd. (Dissolved product of 50% of decamethylcyclopentasiloxane and 50% of silicone resin)
(note 5)
KSP-411 available from Shin-Etsu Chemical Co., Ltd. (Composite powder including a silicone rubber coated with a silicone resin and having an average particle diameter of 12 μm)
(note 6)
KSP-590 available from Shin-Etsu Chemical Co., Ltd.

Production Method

Components to 10 were uniformly mixed by a roller treatment. To this mixture, components 11 to 17 were added and uniformly mixed, to obtain a nonaqueous mousse foundation.

It was confirmed that the foundation obtained as described above had an appearance which was firmly hardened like a mousse, had light spread and extension, and had excellent feeling of use including no stickiness or oily feeling, and very good make-up durability. Further, the foundation did not cause exudation of oil and the like depending on temperature or time and had excellent stability.

(Example 8) Aqueous Eye Wrinkle Cream

In accordance with formulation shown in Table an aqueous eye wrinkle cream was prepared.

TABLE 9

| | Component | Example 8 |
|---|---|---|
| 1 | Crosslinked polyether-modified silicone (note 1) | 5.0 |
| 2 | Crosslinked alkyl-modified dimethylpolysiloxane (note 2) | 7.0 |
| 3 | Crosslinked dimethylpolysiloxane (note 3) | 55.0 |
| 4 | Decamethylcyclopentasiloxane | 8.0 |
| 5 | Sx in Production Example 3 | 6.0 |
| 6 | Jojoba oil | 2.0 |

TABLE 9-continued

| | Component | Example 8 |
|---|---|---|
| 7 | Spherical silicone resin composite powder (note 4) | 12.0 |
| 8 | Highly polymerized dimethylpolysiloxane (note 5) | 5.0 |
| | Total | 100.0 |

(note 1)
KSG-210 available from Shin-Etsu Chemical Co., Ltd. (Mixture of 80% of dimethylpolysiloxane and 20% of POE-crosslinked silicone elastomer)
(note 2)
KSG-41A available from Shin-Etsu Chemical Co., Ltd. (Mixture of 75% of mineral oil and 25% of alkyl-modified silicone elastomer)
(note 3)
KSG-15 available from Shin-Etsu Chemical Co., Ltd. (Mixture of 93% of decamethylcyclopentasiloxane and 7% of silicone elastomer)
(note 4)
KSP-101 available from Shin-Etsu Chemical Co., Ltd. (Composite powder including a silicone rubber coated with a silicone resin and having an average particle diameter of 12 μm)
(note 5)
KF-9028 available from Shin-Etsu Chemical Co., Ltd. (Dissolved product of 80% of decamethylcyclopentasiloxane and 20% of silicone gum)

Production Method

A: Components 1 to 8 were uniformly mixed to obtain an eye wrinkle cream.

It was found that the eye wrinkle cream obtained as described above had light spread and extension, gave a feeling of use including no stickiness, no oily feeling, and wetting feeling and good compatibility with the skin, did not vary depending on temperature or time, and had excellent stability.

(Example 9) Rinse-Off Pack Cosmetic

In accordance with formulation shown in Table 10, a rinse-off pack cosmetic was prepared.

TABLE 10

| | Component | Example 9 |
|---|---|---|
| 1 | Dimethylpolysiloxane (6 cs) | 3.0 |
| 2 | Sx in Production Example 1 | 3.0 |
| 3 | Silicone-branched polyglycerol-modified silicone (note 1) | 2.0 |
| 4 | Kaolin | 30.0 |
| 5 | Carboxyvinyl polymer | 0.4 |
| 6 | 1,3-BG | 10.0 |
| 7 | Glycerol | 20.0 |
| 8 | Preservative | 0.1 |
| 9 | Perfume | 0.1 |
| 10 | Purified water | 31.4 |
| | Total | 100.0 |

(note 1)
KF-6100 available from Shin-Etsu Chemical Co., Ltd.

Production Method

A: Components 1 to 3 and 8 were mixed.
B: Components 5 to 7 and 10 were uniformly mixed, and components 4 and 9 were then mixed and stirred.
C: To B, A was added and emulsified, to obtain a paste-like rinse-off pack cosmetic.

It was found that the rinse-off pack cosmetic obtained as described above had light spread and extension during application, had excellent cleaning effect, very excellent feeling of use that included a wetting feeling and no stickiness and imparted a smooth touch to the skin, and excellent stability.

(Example 10) Eye Color Product

In accordance with formulation shown in Table 11, an eye color product was prepared.

TABLE 11

| | Component | Example 10 |
|---|---|---|
| 1 | Isododecane | 25.5 |
| 2 | (alkyl acrylate/dimethicone) copolymer solution (note 1) | 20.0 |
| 3 | Long-chain alkyl-containing acrylic-silicone resin (note 2) | 2.0 |
| 4 | Hybrid silicone composite powder (note 3) | 6.0 |
| 5 | Trimethyl trimethicone (note 4) | 3.0 |
| 6 | Sx in Production Example 2 | 5.0 |
| 7 | Vaseline | 5.0 |
| 8 | Alkyl-modified-partially crosslinked polyether-modified silicone swelling composition (note 5) | 5.0 |
| 9 | Amorphous silicic anhydride (note 6) | 1.0 |
| 10 | Barium sulfate | 5.0 |
| 11 | Organic color pigment | 0.2 |
| 12 | Alkyl/silicone branched type silicone-treated yellow iron oxide (note 7) | 1.0 |
| 13 | Alkyl/silicone branched type silicone-treated titanium oxide (note 7) | 1.0 |
| 14 | Titanium mica treated with alkyl/silicone branched type silicone (note 8) | 20.0 |
| 15 | Tocopherol | 0.2 |
| 16 | Perfume | 0.1 |
| | Total | 100.0 |

(note 1)
KP-550 available from Shin-Etsu Chemical Co., Ltd. (Dissolved product of 60% of isododecane and 40% of acrylic-silicone)
(note 2)
KP-561P available from Shin-Etsu Chemical Co., Ltd. (Silicone wax having a melting point of 30° C.)
(note 3)
KSP-441 available from Shin-Etsu Chemical Co., Ltd. (Composite powder including an alkyl-modified silicone rubber coated with a silicone resin and having an average particle diameter of 12 μm)
(note 4)
TMF-1.5 available from Shin-Etsu Chemical Co., Ltd.
(note 5)
KSG-320 available from Shin-Etsu Chemical Co., Ltd. (Mixture of 75% of isododecane and 25% of alkyl-modified POE-crosslinked silicone elastomer)
(note 6)
surface-hydrophobized fumed silica: AEROSIL R-972 available from Nippon Aerosil Co., Ltd.
(note 7)
KTP-09W and Y available from Shin-Etsu Chemical Co., Ltd. (KF-9909 treatment color inorganic pigment, W: white, Y: yellow)
(note 8)
KF-9909 available from Shin-Etsu Chemical Co., Ltd.

Production. Method

A: Components 1 to 9 were mixed and uniformly dispersed.
B: To the mixture obtained in A, components 10 to 16 were added and uniformly dispersed, to obtain an eye color product.

The eye color product obtained as described above had good removability, light spread and extension, and a feeling of use including no oily or powdery feeling. It was confirmed that the eye color product had good water resistance, water repellency, and perspiration resistance, and high dura- bility, was unlikely to cause make-up to smear, did not vary depending on temperature change or time, and had excellent stability.

(Example 11) Eyeliner

In accordance with formulation shown in Table 12, an eyeliner was prepared.

TABLE 12

| | Component | Example 11 |
|---|---|---|
| 1 | Sx in Production Example 2 | 22.0 |
| 2 | Dimethylpolysiloxane (6 cs) | 5.0 |
| 3 | Crosslinked alkyl-modified dimethylpolysiloxane (note 1) | 5.0 |
| 4 | Jojoba oil | 2.0 |
| 5 | Silicone-branched alkyl polyether-co-modified silicone (note 2) | 3.0 |
| 6 | Silicone-treated black iron oxide (note 3) | 20.0 |
| 7 | Ethanol | 5.0 |
| 8 | Preservative | 0.1 |
| 9 | Purified water | 37.9 |
| | Total | 100.0 |

(note 1)
KSG-42A available from Shin-Etsu Chemical Co., Ltd. (Mixture of 80% of isododecane and 20% of alkyl-modified silicone elastomer)
(note 2)
KF-6038 available from Shin-Etsu Chemical Co., Ltd.
(note 3)
treated by KF-9901 available from Shin-Etsu Chemical Co., Ltd.

Production Method

A: Components 1 to 5 were warmed and mixed, and a component 6 was added and dispersed uniformly.
B: Components 7 to 9 were warmed and dissolved.
C: To A, B was gradually added with stirring, and emulsified, to obtain an eyeliner.

It was found that the eyeliner obtained as described above had a light spread, gave a feeling of use including no oily or powdery feeling, and wetting and dry feeling, had good water resistance, water repellency, and perspiration resistance, and high durability, was unlikely to cause make-up to smear, did not vary depending on temperature or time, and had excellent stability.

(Example 12) W/O Cleansing Cream

In accordance with formulation shown in Table 13, a W/O cleansing cream was prepared.

TABLE 13

| | Component | Example 12 |
|---|---|---|
| 1 | Dimethylpolysiloxane (6 cs) | 10.0 |
| 2 | Methylphenylpolysiloxane | 15.0 |
| 3 | Liquid paraffin | 8.0 |
| 4 | Isostearic acid | 1.0 |
| 5 | Sx in Production Example 1 | 11.0 |
| 6 | Dextrin fatty acid ester | 0.8 |
| 7 | Polyether-modified silicone (note 1) | 4.0 |
| 8 | Glycerol | 10.0 |
| 9 | Sodium citrate | 0.2 |
| 10 | Sodium chloride | 1.0 |

TABLE 13-continued

| | Component | Example 12 |
|---|---|---|
| 11 | Preservative | 0.1 |
| 12 | Perfume | 0.1 |
| 13 | Purified water | 38.8 |
| | Total | 100.0 |

(note 1)
KF-6017 available from Shin-Etsu Chemical Co., Ltd.

Production Method

A: Components 1 to 7 was heated and mixed.
B: Components 8 to 11 and 13 were heated and dissolved.
C: To A, B was gradually added with stirring, emulsified, and then cooled, and a component 12 was added to obtain a cleansing cream.

It was found that the cleansing cream obtained as described above had fine texture, light spread and extension, gave a feeling of use including no stickiness or oily feeling, and wetting, fresh, and dry feelings, had high cleansing effect, did not vary depending on temperature or time, and had excellent stability.

(Example 13) Lip Cream

In accordance with formulation shown in Table 14, a lip cream was prepared.

TABLE 14

| | Component | Example 13 |
|---|---|---|
| 1 | Palmitic acid/dextrin ethylhexanoate (note 1) | 9.0 |
| 2 | Sx in Production Example 2 | 7.0 |
| 3 | Dissolved product of acrylic-silicone in D5 (note 2) | 5.0 |
| 4 | Alkyl-modified crosslinked dimethylpolysiloxane (note 3) | 8.0 |
| 5 | Alkyl-modified branched polyglycerol-modified silicone (note 4) | 2.0 |
| 6 | Decamethylcyclopentasiloxane | 46.0 |
| 7 | 1,3-butylene glycol | 5.0 |
| 8 | Purified water | 10.8 |
| 9 | Colorant | 1.2 |
| 10 | Titanium oxide-coated mica | 6.0 |
| | Total | 100.0 |

(note 1)
Rheopearl TT available from Chiba Flour Milling Co., Ltd.
(note 2)
KP-545 available from Shin-Etsu Chemical Co., Ltd. (Dissolved product of 70% of decamethylcyclopentasiloxane and 30% of acrylic- silicone)
(note 3)
KSG-43 available from Shin-Etsu Chemical Co., Ltd. (Mixture of 70% of triethylhexanoine and 30% of alkyl-modified silicone elastomer)
(note 4)
KF-6105 available from Shin-Etsu Chemical Co., Ltd.

Production Method

A: In a part of a component 2, a component 9 was mixed and dispersed with a roller mill, and the obtained dispersion, a component 1, a balance of the component 2, and components 3 to 6 were heated and mixed up.
B: Components 7 and 8 were heated and mixed to the mixture obtained in A, emulsified, and then cooled.
C: To the emulsified product obtained in B, a component 10 was added to obtain a lip cream.

The obtained lip cream had a light spread, and no stickiness or oily feeling, and a highly durable film was formed on the lip.

(Example 14) Mascara

In accordance with formulation shown in Table 15, a mascara was prepared.

TABLE 15

| | Component | Example 14 |
|---|---|---|
| 1 | Branched polyether-modified silicone (note 1) | 1.0 |
| 2 | Dimethyldistearylammonium hectorite | 4.0 |
| 3 | Isododecane | 39.5 |
| 4 | Dissolved product of acrylic-silicone in isododecane (note 2) | 20.0 |
| 5 | Palmitic acid/dextrin ethylhexanoate (note 3) | 3.0 |
| 6 | Ceresin | 2.5 |
| 7 | Long-chain alkyl-containing acrylic-silicone resin (note 4) | 2.0 |
| 8 | Beeswax | 2.5 |
| 9 | Sx in Production Example 2 | 5.0 |
| 10 | Hydrogenated lecithin | 0.5 |
| 11 | Silica | 3.0 |
| 12 | Talc | 12.0 |
| 13 | Hydrophobized colorant (note 5) | 5.0 |
| | Total | 100.0 |

(note 1)
KF-6028P available from Shin-Etsu Chemical Co., Ltd.
(note 2)
KP-550 available from Shin-Etsu Chemical Co., Ltd. (Dissolved product of 60% of isododecane and 40% of acrylic-silicone)
(note 3)
Rheopearl TT available from Chiba Flour Milling Co., Ltd.
(note 4)
KP-562P available from Shin-Etsu Chemical Co., Ltd. (Silicone wax having a melting point of 50° C.)
(note 5)
KTP-09B available from Shin-Etsu Chemical Co., Ltd. (KF-9909 treated color inorganic pigment, B: black)

Production Method

A: Components 1 to 3 were uniformly mixed.
B: Components 4 to 10 were heated, stirred, and dissolved, and the mixture obtained in A and pulverized components 11, 12, and 13 were added, uniformly mixed, and then cooled.

The obtained mascara was not sticky, had a light spread, was easily applied to the eyelash, and had very good make-up durability.

(Example 15) Cleansing Oil

In accordance with formulation shown in Table 16, a cleansing oil was prepared.

TABLE 16

| | Component | Example 15 |
|---|---|---|
| 1 | Mineral oil | 30.0 |
| 2 | Isopropyl myristate | 2.0 |
| 3 | Sx in Production Example 1 | 54.9 |
| 4 | PEG-6 diisostearate | 1.0 |
| 5 | Tocopherol acetate | 0.1 |

TABLE 16-continued

| | Component | Example 15 |
|---|---|---|
| 6 | PEG-20 glyceryl triisostearate | 10.0 |
| 7 | Glycerol | 1.0 |
| 8 | Purified water | 1.0 |
| | Total | 100.0 |

Production Method

A: Components 1 to 6 were uniformly mixed,
B: Components 7 and 8 were stirred, dissolved, added to the mixture obtained in A, and uniformly mixed, to obtain a cleansing oil.

The obtained cleansing oil was not sticky, formed a uniform oily film, was easily spread, and had very high cleaning effect.

(Examples 16 and 17) Deodorant Stick

In accordance with formulation shown in Table 17, a deodorant stick was prepared.

TABLE 17

| | Component | Example 16 | Example 17 |
|---|---|---|---|
| 1 | Chlorohydroxy aluminum | 23.0 | 23.0 |
| 2 | Sx in Production Example 1 | 36.5 | — |
| 3 | Sx in Production Example 2 | — | 36.5 |
| 4 | Stearyl alcohol | 8.0 | 8.0 |
| 5 | Talc | 14.88 | 14.88 |
| 6 | Perfume | 0.1 | 0.1 |
| 7 | BHT (dibutylhydroxytoluene) | 0.02 | 0.02 |
| 8 | Paraffin (solid) | 2.0 | 2.0 |
| 9 | Mineral oil | 14.5 | 14.5 |
| 10 | Alkyl-modified-silicone activator (note 1) | 1.0 | 1.0 |
| | Total | 100.0 | 100.0 |

(note 1)
KF-6048 available from Shin-Etsu Chemical Co., Ltd.

Production Method

A: Components 2 to 4 and 7 to 10 were heated, dissolved, and mixed.
B: Components 1 and 5 were uniformly mixed in A to be uniformly dispersed and mixed with a mixer.
C: A component 6 was added and uniformly mixed.
D: The mixture was placed in a mold, cooled, and solidified.

A feeling of use of the deodorant sticks in Examples 16 and 17 was evaluated. The results are shown in Table 18.

Method for Evaluating Feeling of Use

Ten experts actually used the deodorant sticks to evaluate the feeling of use thereof.

Evaluation Criteria

Decision was performed in accordance with the following criteria.
excellent: Five or more experts decided that the feeling of use was good.
good: Three or more experts decided that the feeling of use was good.
poor: Less than three experts decided that the feeling of use was good.

TABLE 18

| | Example 16 | Example 17 |
|---|---|---|
| Dry feeling | good | excellent |
| Sticky feeling | good | excellent |
| Deodorization effect | excellent | excellent |

It is found that in Examples 16 and 17 that are deodorants of the present invention, excessive dry feeling and sticky feeling are not produced and the persistence of deodorization effect is excellent.

(Example 18) Deodorant Spray

In accordance with formulation shown in Table 19, a deodorant spray was prepared.

TABLE 19

| | Component | Example 18 |
|---|---|---|
| 1 | Chlorohydroxy aluminum | 30.0 |
| 2 | Silicic anhydride | 15.0 |
| 3 | Sx in Production Example 1 | 10.0 |
| 4 | Silicone-treated talc (note 1) | 14.88 |
| 5 | Perfume | 0.1 |
| 6 | BHT (dibutylhydroxytoluene) | 0.02 |
| 7 | Zinc Oxide | 5.0 |
| 8 | Triclosan | 0.1 |
| 9 | Isopropyl myristate | 21.9 |
| 10 | Silicone activator (note 2) | 3.0 |
| | Total | 100.0 |

(note 1)
treated with KF-9909 available from Shin-Etsu Chemical Co., Ltd.
(note 2)
KF-6105 available from Shin-Etsu Chemical Co., Ltd.

Production Method

A: Components 2 to 4 and 6 to 10 were uniformly mixed.
B: A component 1 was uniformly mixed in A to be uniformly dispersed and mixed with a mixer.
C: A component 5 was added and uniformly mixed.
D: A spray container was filled with 10 parts of the raw liquid component C and 90 parts of LPG.

A feeling of use of the deodorant spray in Example 18 was evaluated. The results are shown in Table 20.

Method for Evaluating Feeling of Use

Ten experts actually used the deodorant spray to evaluate the feeling of use thereof.

Evaluation Criteria

Decision was performed in accordance with the following criteria.
excellent: Five or more experts decided that the feeling of use was good.
good: Three or more experts decided that the feeling of use was good.
poor: Less than three experts decided that the feeling of use was good.

TABLE 20

|  | Example 18 |
| --- | --- |
| Dry feeling | excellent |
| Sticky feeling | excellent |
| Deodorization effect | excellent |

It is found that in Example 18 that is a deodorant of the present invention, excessive dry feeling and sticky feeling are not produced and the persistence of deodorization effect is excellent.

(Example 19) Nonaqueous Deodorant Cream

In accordance with formulation shown in Table 21, a nonaqueous deodorant cream was prepared

TABLE 21

|  | Component | Example 19 |
| --- | --- | --- |
| 1 | Aluminum zirconium trichlorohydrex glycine | 19.0 |
| 2 | Sx in Production Example 2 | 30.0 |
| 3 | Silicone elastomer (note 1) | 21.5 |
| 4 | Silicone composite powder (note 2) | 10.0 |
| 5 | Neopentyl glycol dioctanoate | 9.68 |
| 6 | Perfume | 0.1 |
| 7 | BHT (dibutylhydroxytoluene) | 0.02 |
| 8 | Citric acid | 0.1 |
| 9 | Benzyl alcohol | 0.1 |
| 10 | Dimethylsilylated silica | 0.5 |
| 11 | Polyethylene | 3.0 |
| 12 | Ceresin | 6.0 |
|  | Total | 100.0 |

(note 1)
KSG-15 available from Shin-Etsu Chemical Co., Ltd. (Mixture of 93% of decamethylcyclopentasiloxane and 7% of silicone elastomer)
(note 2)
KSP-100 available from Shin-Etsu Chemical Co., Ltd. (Composite powder including a silicone rubber coated with a silicone resin and having an average particle diameter of 5 μm)

Production Method

A: Components 2, 3, 5, 7, 9, 11, and 12 were heated and uniformly mixed.
B: A component 10 was uniformly mixed in A to be uniformly dispersed and mixed with a mixer.
C: Components 1, 4, and 8 were added to B, and uniformly mixed.
D: A component 6 was added to C, and uniformly mixed, and the mixture was then placed in a container.

In Example 19 described above, the nonaqueous deodorant cream was very smoothly applied and spread, had a good extension and no excessive dry feeling or sticky feeling, and was excellent in persistence of deodorization effect.

(Example 20) W/O Deodorant Cream

In accordance with formulation shown in Table 22, a W/O deodorant cream was prepared.

TABLE 22

|  | Component | Example 20 |
| --- | --- | --- |
| 1 | Silicone-emulsified elastomer (note 1) | 3.0 |
| 2 | Silicone elastomer (note 2) | 2.0 |
| 3 | Polyether-modified silicone (note 3) | 2.0 |
| 4 | Ethylhexyl palmitate | 5.0 |
| 5 | Isopropyl methylphenol | 0.1 |
| 6 | Chlorohydroxy aluminum | 5.0 |
| 7 | Benzalkonium chloride | 0.1 |
| 8 | Sx in Production Example 2 | 15.0 |
| 9 | Glycerol | 5.0 |
| 10 | 1,3-BG | 5.0 |
| 11 | Ethanol | 5.0 |
| 12 | Phenoxyethanol | 0.3 |
| 13 | Purified water | 52.5 |
|  | Total | 100.0 |

(note 1)
KSG-210 available from Shin-Etsu Chemical Co., Ltd. (Mixture of 80% of dimethylpolysiloxane and 20% of POE-crosslinked silicone elastomer)
(note 2)
KSG-15 available from Shin-Etsu Chemical Co., Ltd. (Mixture of 93% of decamethylcyclopentasiloxane and 7% of silicone elastomer)
(note 3)
KF-6028P available from Shin-Etsu Chemical Co., Ltd.

Production Method

A: Components 1 to 4 and 8 were uniformly mixed.
B: Components 5 to 7 were uniformly mixed in A to be uniformly dispersed and mixed with a mixer.
C: Components 9 to 13 were dissolved.
D: B was added to A, and emulsified, and then the resultant was placed in a container.

In Example 20 described above, the W/O deodorant cream had a fresh feeling of use, was very smoothly applied and spread, had a good extension and no excessive dry feeling or sticky feeling during use, and was excellent in persistence of deodorization effect.

The present invention is not limited to the aforementioned embodiments. The embodiments are examples, and any examples that have substantially the same configuration and demonstrate the same effects as the technical concept described in claims of the present invention are included in the technical scope of the present invention.

The invention claimed is:

1. A cosmetic comprising only one cyclic silicone, wherein said cyclic silicone is represented by the following general formula (1), has a boiling point of 205 to 255° C. and has a viscosity of less than 5 mm²/s (25° C.),

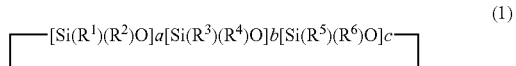

(1)

wherein $R^1$ is a monovalent hydrocarbon group having 2 or 3 carbon atoms, $R^2$, $R^3$, $R^4$, $R^5$, and $R^6$ are each independently a monovalent hydrocarbon group having 1 to 3 carbon atoms;
"a" is a positive number satisfying 0<a<4, and "b" and "c" are each independently a number of 0 to 3, provided that (a+b+c)≤4, and
further comprising an organic ultraviolet absorber.

2. The cosmetic according to claim 1, wherein the cyclic silicone is selected from the group consisting of 1,3-dipropyl-1,3,5,5-tetramethylcyclotrisiloxane, 1,3,5-tripropyl-1,3,5-trimethylcyclotrisiloxane, 1,3,5,5-tetraethyl-1,3-dimethylcyclotrisiloxane, 1,3,3,5,5-pentaethyl-1- methylcyclotrisiloxane, 1,1,3,3,5,5-hexaethylcyclotrisiloxane, 1-propyl-1,3,3,5,5,7,7-heptamethylcyclotetrasiloxane, 1-ethyl-1,3,3,5,5,7,7-heptamethylcyclotetrasiloxane, 1,3-diethyl-1,3,5,5,7,7-hexamethylcyclotetrasiloxane, 1,3,5-triethyl-1,3,5,7,7-pentamethylcyclotetrasiloxane, and 1,3,5,7-tetraethyl-1,3,5,7-tetramethylcyclotetrasiloxane.

3. The cosmetic according to claim 2, wherein the organic ultraviolet absorber is one or more selected from the group consisting of ethylhexyl methoxycinnamate, diethylamino hydroxybenzoyl hexyl benzoate, octyl salicylate, polysilicone-15, t-butyl methoxydibenzoylmethane, oxybenzone, methylene bis-benzotriazolyl tetramethylbutylphenol, bis-ethylhexyloxyphenol methoxyphenyl triazine, and octocrylene.

4. The cosmetic according to claim 3, further comprising an oily component being solid at 25° C.

5. The cosmetic according to claim 4, wherein the oily component being solid at 25° C. is one or more selected from the group consisting of a polyethylene, ceresin, ozokerite, beeswax, microcrystalline wax, stearyl alcohol, behenyl alcohol, and cetanol.

6. The cosmetic according to claim 2, further comprising an oily component being solid at 25° C.

7. The cosmetic according to claim 6, wherein the oily component being solid at 25° C. is one or more selected from the group consisting of a polyethylene, ceresin, ozokerite, beeswax, microcrystalline wax, stearyl alcohol, behenyl alcohol, and cetanol.

8. The cosmetic according to claim 1, wherein the organic ultraviolet absorber is one or more selected from the group consisting of ethylhexyl methoxycinnamate, diethylamino hydroxybenzoyl hexyl benzoate, octyl salicylate, polysilicone-15, t-butyl methoxydibenzoylmethane, oxybenzone, methylene bis-benzotriazolyl tetramethylbutylphenol, bis-ethylhexyloxyphenol methoxyphenyl triazine, and octocrylene.

9. The cosmetic according to claim 8, further comprising an oily component being solid at 25° C.

10. The cosmetic according to claim 9, wherein the oily component being solid at 25° C. is one or more selected from the group consisting of a polyethylene, ceresin, ozokerite, beeswax, microcrystalline wax, stearyl alcohol, behenyl alcohol, and cetanol.

11. The cosmetic according to claim 1, further comprising an oily component being solid at 25° C.

12. The cosmetic according to claim 11, wherein the oily component being solid at 25° C. is one or more selected from the group consisting of a polyethylene, ceresin, ozokerite, beeswax, microcrystalline wax, stearyl alcohol, behenyl alcohol, and cetanol.

\* \* \* \* \*